United States Patent
Hirotsuka et al.

(10) Patent No.: US 8,371,307 B2
(45) Date of Patent: Feb. 12, 2013

(54) METHODS AND DEVICES FOR THE TREATMENT OF AIRWAY OBSTRUCTION, SLEEP APNEA AND SNORING

(75) Inventors: Mark Hirotsuka, San Jose, CA (US); Jasper Jackson, Newark, CA (US); Damien Shulock, San Francisco, CA (US); Andrew Frazier, Sunnyvale, CA (US); Chad Roue, San Jose, CA (US); Erik van der Burg, Los Gatos, CA (US); Michael Dineen, Portola Valley, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 706 days.

(21) Appl. No.: 11/835,966

(22) Filed: Aug. 8, 2007

(65) Prior Publication Data
US 2008/0053461 A1 Mar. 6, 2008

Related U.S. Application Data (63) Continuation-in-part of application No. 11/349,040, filed on Feb. 7, 2006, now Pat. No. 7,975,700.

(60) Provisional application No. 60/836,578, filed on Aug. 8, 2006, provisional application No. 60/650,867, filed on Feb. 8, 2005, provisional application No. 60/726,028, filed on Oct. 12, 2005.

(51) Int. Cl.
*A61F 5/56* (2006.01)

(52) U.S. Cl. ............ 128/848; 606/232; 606/286

(58) Field of Classification Search ............ 128/848, 128/846; 606/232, 258, 286, 310, 319; 623/13.14, 623/22.36, 22.37, 23.26, 23.27; 433/225; 411/446, 519; 600/375
See application file for complete search history.

(56) References Cited

U.S. PATENT DOCUMENTS

| | | | |
|---|---|---|---|
| 346,771 A | 8/1886 | Phillips |
| 1,156,440 A | 10/1915 | Smith |
| 1,374,963 A | 4/1921 | Stevenson |
| 2,154,428 A | 4/1939 | Andres |
| 2,181,746 A | 11/1939 | Siebrandt |
| 2,583,896 A | 1/1952 | Siebrandt |
| 2,824,717 A | 2/1958 | Yeager |
| 2,966,907 A | 1/1961 | Fasolino |
| 3,477,429 A | 11/1969 | Sampson |
| 3,593,709 A | 7/1971 | Halloran |
| 4,263,904 A | 4/1981 | Judet |
| 4,279,248 A | 7/1981 | Gabbay |

(Continued)

FOREIGN PATENT DOCUMENTS

| | | |
|---|---|---|
| CN | 101040807 | 9/2007 |
| DE | 1 242 322 | 6/1967 |

(Continued)

OTHER PUBLICATIONS

Letter to Aspire Medical, Inc. from a third party, dated Jul. 13, 2007 (redacted in part).

(Continued)

*Primary Examiner* — Kevin C Sirmons
*Assistant Examiner* — Keri J Nelson (57) ABSTRACT

Methods and devices for the treatment of airway obstruction, sleep apnea and snoring are disclosed. In some embodiments, a glossal suspension system includes a tissue tensioner that includes a suture loop made of one or more sutures configured to suspend the tongue with at least one portion configured to extend laterally through the tongue, and a securement mechanism configured to be attached to a patient's mandible that includes one more adjustment assemblies for engaging the one or more sutures and adjusting tension on the suture loop. Various tethers and anchors that can be used with the glossal suspension system are also disclosed.

13 Claims, 7 Drawing Sheets

U.S. PATENT DOCUMENTS

| | | |
|---|---|---|
| 4,348,179 A | 9/1982 | Nardella |
| 4,366,815 A | 1/1983 | Broomes |
| 4,676,240 A | 6/1987 | Gardy |
| 4,700,697 A | 10/1987 | Mundell |
| 4,830,008 A | 5/1989 | Meer |
| 4,840,172 A | 6/1989 | Augustine |
| 4,858,601 A | 8/1989 | Glisson |
| 4,885,824 A | 12/1989 | Schwab |
| 4,898,156 A | 2/1990 | Gatturna |
| 4,978,323 A | 12/1990 | Freedman |
| 5,046,513 A | 9/1991 | Gatturna |
| 5,123,425 A | 6/1992 | Shannon, Jr. |
| 5,127,413 A | 7/1992 | Ebert |
| 5,176,617 A | 1/1993 | Fischell |
| 5,176,618 A | 1/1993 | Freedman |
| 5,178,156 A | 1/1993 | Takishima |
| 5,190,546 A | 3/1993 | Jervis |
| 5,192,303 A | 3/1993 | Gatturna |
| 5,254,097 A | 10/1993 | Schock et al. |
| 5,282,845 A | 2/1994 | Bush |
| 5,320,602 A | 6/1994 | Karpiel et al. |
| 5,358,511 A | 10/1994 | Gatturna |
| 5,411,522 A | 5/1995 | Trott |
| 5,443,482 A | 8/1995 | Stone |
| 5,460,524 A | 10/1995 | Anderson |
| 5,462,561 A | 10/1995 | Voda |
| 5,464,424 A | 11/1995 | O'Donnell, Jr. |
| 5,478,353 A | 12/1995 | Yoon |
| 5,501,696 A | 3/1996 | Trott |
| 5,505,735 A | 4/1996 | Li |
| 5,512,037 A | 4/1996 | Russell et al. |
| 5,522,844 A | 6/1996 | Johnson |
| 5,554,171 A | 9/1996 | Gatturna |
| 5,571,104 A | 11/1996 | Li |
| 5,573,540 A | 11/1996 | Yoon |
| 5,578,032 A | 11/1996 | Lalonde |
| 5,620,012 A | 4/1997 | Benderev et al. |
| 5,626,597 A | 5/1997 | Urban et al. |
| 5,647,874 A | 7/1997 | Hayhurst |
| 5,662,654 A | 9/1997 | Thompson |
| 5,665,089 A | 9/1997 | Dall |
| 5,690,640 A | 11/1997 | Gotfried |
| 5,718,705 A | 2/1998 | Sammarco |
| 5,722,976 A | 3/1998 | Brown |
| 5,725,557 A | 3/1998 | Gatturna |
| 5,735,875 A | 4/1998 | Bonutti |
| 5,797,919 A | 8/1998 | Brinson |
| 5,810,824 A | 9/1998 | Chan |
| 5,840,078 A | 11/1998 | Yerys |
| 5,868,762 A | 2/1999 | Cragg |
| 5,893,856 A | 4/1999 | Jacob |
| 5,897,491 A | 4/1999 | Kastenbauer et al. |
| 5,928,231 A | 7/1999 | Klein |
| 5,954,057 A | 9/1999 | Li |
| 5,979,456 A | 11/1999 | Magovern |
| 5,988,171 A | 11/1999 | Sohn |
| 6,042,534 A | 3/2000 | Gellman et al. |
| 6,079,413 A | 6/2000 | Braran |
| 6,132,438 A | 10/2000 | Fleischman |
| 6,161,541 A | 12/2000 | Woodson |
| 6,162,362 A | 12/2000 | Ma |
| 6,188,932 B1 | 2/2001 | Lindegren |
| 6,200,330 B1 | 3/2001 | Benderev |
| 6,203,565 B1 | 3/2001 | Bonutti |
| 6,240,316 B1 | 5/2001 | Richmond |
| 6,306,141 B1 | 10/2001 | Jervis |
| 6,312,431 B1 | 11/2001 | Asfora |
| 6,315,780 B1 | 11/2001 | Lalonde |
| 6,322,492 B1 | 11/2001 | Kovac |
| 6,328,686 B1 | 12/2001 | Kovac |
| 6,328,753 B1 | 12/2001 | Zammit |
| 6,408,851 B1 | 6/2002 | Karell |
| 6,408,852 B2 | 6/2002 | Tielemans |
| 6,423,072 B1 | 7/2002 | Zappala |
| 6,425,900 B1 | 7/2002 | Knodel |
| 6,431,174 B1 | 8/2002 | Knudson |
| 6,439,238 B1 | 8/2002 | Brenzel |
| 6,447,524 B1 | 9/2002 | Knodel |
| 6,458,100 B2 | 10/2002 | Roue |
| 6,482,178 B1 | 11/2002 | Andrews |
| 6,503,267 B2 | 1/2003 | Bonutti |
| 6,536,439 B1 | 3/2003 | Palmisano |
| 6,540,695 B1 | 4/2003 | Burbank |
| 6,554,833 B2 | 4/2003 | Levy |
| 6,599,311 B1 | 7/2003 | Biggs |
| 6,626,910 B1 | 9/2003 | Hugues |
| 6,626,916 B1 | 9/2003 | Yeung et al. |
| 6,634,362 B2 | 10/2003 | Conrad |
| 6,656,182 B1 | 12/2003 | Hayhurst |
| 6,668,834 B1 | 12/2003 | Zikria |
| 6,685,707 B2 | 2/2004 | Roman |
| 6,746,472 B2 | 6/2004 | Frazier |
| 6,770,022 B2 | 8/2004 | Mechlenburg |
| 6,913,607 B2 | 7/2005 | Ainsworth |
| 6,955,172 B2 | 10/2005 | Nelson |
| 6,971,396 B2 | 12/2005 | Knudson |
| 6,997,189 B2 | 2/2006 | Biggs |
| 7,008,428 B2 | 3/2006 | Cachia |
| 7,017,582 B2 | 3/2006 | Metzger |
| 7,022,131 B1 | 4/2006 | Derowe |
| 7,025,756 B2 | 4/2006 | Frazier |
| 7,028,691 B2 | 4/2006 | Knudson |
| 7,036,515 B2 | 5/2006 | Conrad |
| 7,047,979 B2 | 5/2006 | Conrad |
| 7,048,682 B2 | 5/2006 | Neisz |
| 7,052,498 B2 | 5/2006 | Levy |
| 7,055,525 B2 | 6/2006 | l'Estrange |
| 7,060,021 B1 | 6/2006 | Wilk |
| 7,062,317 B2 | 6/2006 | Avrahami |
| 7,063,089 B2 | 6/2006 | Knudson |
| 7,073,505 B2 | 7/2006 | Nelson |
| 7,077,143 B2 | 7/2006 | Knudson |
| 7,077,144 B2 | 7/2006 | Knudson |
| 7,090,672 B2 | 8/2006 | Underwood |
| 7,090,690 B2 | 8/2006 | Foerster |
| 7,100,613 B2 | 9/2006 | Conrad |
| 7,107,992 B2 | 9/2006 | Brooks |
| 7,115,110 B2 | 10/2006 | Frazier |
| 7,122,043 B2 | 10/2006 | Greenhalgh |
| 7,128,753 B1 | 10/2006 | Bonutti |
| 7,131,973 B2 | 11/2006 | Hoffman |
| 7,144,363 B2 | 12/2006 | Pai |
| 7,146,981 B2 | 12/2006 | Knudson |
| 7,150,680 B2 | 12/2006 | White |
| 7,150,750 B2 | 12/2006 | Damarati |
| 7,160,309 B2 | 1/2007 | Voss |
| 7,164,942 B2 | 1/2007 | Avrahami |
| D536,792 S | 2/2007 | Krueger |
| 7,184,842 B2 | 2/2007 | Seifert |
| 7,186,255 B2 | 3/2007 | Baynham |
| 7,186,262 B2 | 3/2007 | Saadat |
| 7,188,627 B2 | 3/2007 | Nelson |
| 7,191,015 B2 | 3/2007 | Lamson |
| 7,198,595 B2 | 4/2007 | Hegde |
| 7,201,771 B2 | 4/2007 | Lane |
| 7,213,599 B2 | 5/2007 | Conrad |
| 7,216,648 B2 | 5/2007 | Nelson |
| 7,226,408 B2 | 6/2007 | Harai |
| 7,229,417 B2 | 6/2007 | Foerster |
| 7,229,453 B2 | 6/2007 | Anderson |
| 7,237,553 B2 | 7/2007 | Knudson |
| 7,237,554 B2 | 7/2007 | Conrad et al. |
| 7,238,200 B2 | 7/2007 | Lee |
| 7,247,164 B1 | 7/2007 | Ritchart |
| 7,255,109 B2 | 8/2007 | Knudson |
| 7,255,110 B2 | 8/2007 | Knudson |
| 7,285,124 B2 | 10/2007 | Foerster |
| 7,288,259 B2 | 10/2007 | Sanders |
| 7,311,103 B2 | 12/2007 | Jeppesen |
| 7,322,356 B2 | 1/2008 | Critzer |
| 7,322,993 B2 | 1/2008 | Metzger |
| 7,328,698 B2 | 2/2008 | Scarberry |
| 7,328,705 B2 | 2/2008 | Abramson |
| RE40,156 E | 3/2008 | Sharps |
| 7,337,781 B2 | 3/2008 | Vassallo |
| 7,347,812 B2 | 3/2008 | Mellier |
| 7,360,542 B2 | 4/2008 | Nelson |

| | | |
|---|---|---|
| 7,361,168 B2 | 4/2008 | Makower |
| 7,363,926 B2 | 4/2008 | Pflueger |
| 7,367,340 B2 | 5/2008 | Nelson |
| 2001/0050084 A1 | 12/2001 | Knudson |
| 2001/0050085 A1 | 12/2001 | Knudson |
| 2001/0054426 A1 | 12/2001 | Knudson |
| 2001/0054428 A1 | 12/2001 | Knudson |
| 2002/0022841 A1 | 2/2002 | Kovac |
| 2002/0035994 A1 | 3/2002 | Stevens |
| 2002/0087051 A1 | 7/2002 | Levisman |
| 2002/0107525 A1 | 8/2002 | Harari |
| 2002/0157675 A1 | 10/2002 | Clark |
| 2002/0188297 A1 | 12/2002 | Dakin et al. |
| 2003/0065402 A1 | 4/2003 | Anderson |
| 2003/0130670 A1 | 7/2003 | Anderson |
| 2003/0149445 A1 | 8/2003 | Knudson |
| 2003/0149488 A1 | 8/2003 | Metzger |
| 2004/0006339 A1 | 1/2004 | Underwood |
| 2004/0025884 A1 | 2/2004 | McKown |
| 2004/0045555 A1 | 3/2004 | Nelson et al. |
| 2004/0045556 A1 | 3/2004 | Nelson |
| 2004/0049102 A1 | 3/2004 | Nelson |
| 2004/0078054 A1 | 4/2004 | Biggs et al. |
| 2004/0122474 A1 | 6/2004 | Gellman et al. |
| 2004/0134491 A1 | 7/2004 | Pflueger |
| 2004/0138585 A1 | 7/2004 | Dematteis et al. |
| 2004/0149290 A1 | 8/2004 | Nelson |
| 2004/0172054 A1 | 9/2004 | Metzger |
| 2005/0004417 A1 | 1/2005 | Nelson |
| 2005/0092332 A1 | 5/2005 | Conrad |
| 2005/0126563 A1 | 6/2005 | van der Burg et al. |
| 2005/0241646 A1 | 11/2005 | Sotos |
| 2005/0251255 A1 | 11/2005 | Metzger |
| 2005/0267547 A1 | 12/2005 | Knudson |
| 2005/0268919 A1 | 12/2005 | Knudson |
| 2005/0268922 A1 | 12/2005 | Conrad |
| 2005/0268923 A1 | 12/2005 | Knudson |
| 2005/0274387 A1 | 12/2005 | MacKen |
| 2005/0284485 A9 | 12/2005 | Nelson |
| 2006/0005843 A9 | 1/2006 | Nelson |
| 2006/0058792 A1 | 3/2006 | Hynes |
| 2006/0060207 A1 | 3/2006 | Hegde |
| 2006/0070626 A1 | 4/2006 | Frazier |
| 2006/0090762 A1 | 5/2006 | Hegde |
| 2006/0150986 A1 | 7/2006 | Roue et al. |
| 2006/0153876 A1 | 7/2006 | Sanders |
| 2006/0157055 A1 | 7/2006 | Pflueger |
| 2006/0185673 A1 | 8/2006 | Critzer |
| 2006/0185680 A1 | 8/2006 | Bhat |
| 2006/0189971 A1 | 8/2006 | Tasto |
| 2006/0201519 A1 | 9/2006 | Hirotsuka et al. |
| 2006/0207606 A1 | 9/2006 | Roue et al. |
| 2006/0207607 A1 | 9/2006 | Hirotsuka et al. |
| 2006/0207608 A1 | 9/2006 | Hirotsuka et al. |
| 2006/0207612 A1 | 9/2006 | Jackson et al. |
| 2006/0235264 A1 | 10/2006 | Vassallo |
| 2006/0266369 A1 | 11/2006 | Atkinson |
| 2006/0266372 A1 | 11/2006 | Miller |
| 2006/0270889 A1 | 11/2006 | Nelson |
| 2006/0271059 A1 | 11/2006 | Reay-Young |
| 2006/0271060 A1 | 11/2006 | Gordon |
| 2006/0276817 A1 | 12/2006 | Vassallo |
| 2006/0276888 A1 | 12/2006 | Lee |
| 2006/0289014 A1 | 12/2006 | Purdy |
| 2006/0289015 A1 | 12/2006 | Boucher |
| 2006/0293710 A1 | 12/2006 | Foerster |
| 2007/0000497 A1 | 1/2007 | Boucher |
| 2007/0021751 A1 | 1/2007 | Reay-Young |
| 2007/0034210 A1 | 2/2007 | Paraschac |
| 2007/0079833 A1 | 4/2007 | Lamberg |
| 2007/0089756 A1 | 4/2007 | Nelson |
| 2007/0102004 A1 | 5/2007 | Nelson |
| 2007/0102010 A1 | 5/2007 | Lemperle |
| 2007/0119463 A1 | 5/2007 | Nelson |
| 2007/0137654 A1 | 6/2007 | Paraschac |
| 2007/0137655 A1 | 6/2007 | Paraschac |
| 2007/0144531 A1 | 6/2007 | Tomas |
| 2007/0144532 A1 | 6/2007 | Gillis |
| 2007/0144533 A1 | 6/2007 | Nelson |
| 2007/0144534 A1 | 6/2007 | Mery |
| 2007/0144535 A1 | 6/2007 | Hegde |
| 2007/0144539 A1 | 6/2007 | van der Burg et al. |
| 2007/0163603 A1 | 7/2007 | Sikora |
| 2007/0186936 A1 | 8/2007 | Nelson |
| 2007/0193587 A1 | 8/2007 | Boucher |
| 2007/0204866 A1 | 9/2007 | Conrad |
| 2007/0209664 A1 | 9/2007 | Paraschac |
| 2007/0209665 A1 | 9/2007 | Gillis |
| 2007/0227545 A1 | 10/2007 | Conrad |
| 2007/0233276 A1 | 10/2007 | Conrad |
| 2007/0244529 A1 | 10/2007 | Choi |
| 2007/0246052 A1 | 10/2007 | Hegde |
| 2007/0248640 A1 | 10/2007 | Karabey |
| 2007/0255172 A1 | 11/2007 | Pflueger |
| 2007/0256693 A1 | 11/2007 | Paraschac |
| 2007/0261701 A1 | 11/2007 | Sanders |
| 2007/0267027 A1 | 11/2007 | Nelson |
| 2007/0270631 A1 | 11/2007 | Nelson |
| 2007/0270632 A1 | 11/2007 | Nelson |
| 2007/0272257 A1 | 11/2007 | Nelson |
| 2007/0288057 A1 | 12/2007 | Kuhnel |
| 2007/0289600 A1 | 12/2007 | Li |
| 2007/0293727 A1 | 12/2007 | Goldfarb |
| 2007/0293946 A1 | 12/2007 | Gonzales |
| 2008/0015540 A1 | 1/2008 | Muni |
| 2008/0015594 A1 | 1/2008 | Ritchart |
| 2008/0021512 A1 | 1/2008 | Knudson |
| 2008/0023012 A1 | 1/2008 | Dineen et al. |
| 2008/0027480 A1 | 1/2008 | van der Burg et al. |
| 2008/0027560 A1 | 1/2008 | Jackson et al. |
| 2008/0033232 A1 | 2/2008 | Catanese, III |
| 2008/0033488 A1 | 2/2008 | Catanese, III |
| 2008/0035157 A1 | 2/2008 | Yan |
| 2008/0035158 A1 | 2/2008 | Pflueger |
| 2008/0035160 A1 | 2/2008 | Woodson et al. |
| 2008/0039894 A1 | 2/2008 | Catanese, III |
| 2008/0041398 A1 | 2/2008 | Hegde |
| 2008/0046022 A1 | 2/2008 | Bhat |
| 2008/0047566 A1 | 2/2008 | Hegde |
| 2008/0053461 A1 | 3/2008 | Hirotsuka et al. |
| 2008/0060660 A1 | 3/2008 | Nelson |
| 2008/0064984 A1 | 3/2008 | Pflueger |
| 2008/0065209 A1 | 3/2008 | Pflueger |
| 2008/0066764 A1 | 3/2008 | Paraschac |
| 2008/0066765 A1 | 3/2008 | Paraschac |
| 2008/0066766 A1 | 3/2008 | Paraschac |
| 2008/0066767 A1 | 3/2008 | Paraschac |
| 2008/0066769 A1 | 3/2008 | Dineen et al. |
| 2008/0081049 A1 | 4/2008 | Sanders |
| 2008/0097154 A1 | 4/2008 | Makower |
| 2008/0097239 A1 | 4/2008 | Chang |
| 2008/0097295 A1 | 4/2008 | Makower |
| 2008/0097400 A1 | 4/2008 | Chang |
| 2008/0097514 A1 | 4/2008 | Chang |
| 2008/0097515 A1 | 4/2008 | Chang |
| 2008/0097516 A1 | 4/2008 | Chang |
| 2008/0103361 A1 | 5/2008 | Makower |
| 2008/0112981 A1 | 5/2008 | Sanders |
| 2008/0119693 A1 | 5/2008 | Makower |
| 2008/0119875 A1 | 5/2008 | Ino |
| 2008/0125626 A1 | 5/2008 | Chang |
| 2008/0125720 A1 | 5/2008 | Kim |
| 2008/0132938 A1 | 6/2008 | Chang |
| 2008/0208265 A1 | 8/2008 | Frazier et al. |

FOREIGN PATENT DOCUMENTS

| | | |
|---|---|---|
| DE | 29614901 U1 | 10/1996 |
| DE | 20015980 U1 | 3/2001 |
| DE | 10 2005 000 702 | 7/2006 |
| DE | 60029111 T2 | 1/2007 |
| EP | 0295041 | 12/1988 |
| EP | 0702934 | 3/1996 |
| EP | 1159925 | 12/2001 |
| EP | 1216013 | 6/2002 |
| EP | 1604625 | 12/2005 |
| EP | 1239798 | 2/2007 |
| EP | 1342454 | 5/2007 |
| EP | 1797846 | 6/2007 |

| | | |
|---|---|---|
| EP | 1857071 | 11/2007 |
| EP | 1867309 | 12/2007 |
| EP | 0758254 | 1/2008 |
| EP | 1339445 | 5/2008 |
| EP | 1585468 | 7/2008 |
| FR | 2880253 A | 7/1976 |
| JP | 2003265621 | 9/2003 |
| WO | WO9420040 | 9/1994 |
| WO | WO9529716 | 11/1995 |
| WO | WO9730638 | 8/1997 |
| WO | WO9900058 | 1/1999 |
| WO | WO9920339 | 4/1999 |
| WO | WO0066050 | 11/2000 |
| WO | WO0067257 | 11/2000 |
| WO | WO0119301 | 3/2001 |
| WO | WO0128457 | 4/2001 |
| WO | WO0213738 | 2/2002 |
| WO | WO02058564 | 8/2002 |
| WO | WO02062237 | 8/2002 |
| WO | WO02076341 | 10/2002 |
| WO | WO02076352 | 10/2002 |
| WO | WO02076353 | 10/2002 |
| WO | WO02076354 | 10/2002 |
| WO | WO03041612 | 5/2003 |
| WO | WO04000158 | 12/2003 |
| WO | WO2004021870 | 3/2004 |
| WO | WO2004032798 | 4/2004 |
| WO | WO2004064729 | 8/2004 |
| WO | WO2004066847 | 8/2004 |
| WO | WO2004084709 | 10/2004 |
| WO | WO2005044158 | 5/2005 |
| WO | WO2005046554 | 5/2005 |
| WO | WO2005117776 | 12/2005 |
| WO | WO2005122954 | 12/2005 |
| WO | WO2006012188 | 2/2006 |
| WO | WO2006026509 | 3/2006 |
| WO | WO2006034434 | 6/2006 |
| WO | WO2006060594 | 6/2006 |
| WO | WO2006072571 | 7/2006 |
| WO | WO2006076316 | 7/2006 |
| WO | WO2006093533 | 9/2006 |
| WO | WO2006093712 | 9/2006 |
| WO | WO2006093795 | 9/2006 |
| WO | WO2006107401 | 10/2006 |
| WO | WO2006125009 | 11/2006 |
| WO | WO2006128092 | 11/2006 |
| WO | WO2006132948 | 12/2006 |
| WO | WO2007004614 | 1/2007 |
| WO | WO2007009117 | 1/2007 |
| WO | WO2006130505 | 3/2007 |
| WO | WO2007062120 | 5/2007 |
| WO | WO2007064908 | 6/2007 |
| WO | WO2007067724 | 6/2007 |
| WO | WO2007067942 | 6/2007 |
| WO | WO2007075981 | 7/2007 |
| WO | WO2007079055 | 7/2007 |
| WO | WO2007092865 | 8/2007 |
| WO | WO2007095582 | 8/2007 |
| WO | WO2007097924 | 8/2007 |
| WO | WO2007098375 | 8/2007 |
| WO | WO2007103324 | 9/2007 |
| WO | WO2007103800 | 9/2007 |
| WO | WO2007103826 | 9/2007 |
| WO | WO2007106755 | 9/2007 |
| WO | WO2007111636 | 10/2007 |
| WO | WO2007120848 | 10/2007 |
| WO | WO2007120850 | 10/2007 |
| WO | WO2007130880 | 11/2007 |
| WO | WO2007130881 | 11/2007 |
| WO | WO2008014028 | 1/2008 |
| WO | WO2008060317 | 5/2008 |

OTHER PUBLICATIONS

Argamaso, Ravelo, M.D., *Glossopexy for Upper Airway Obstruction in Robin Sequence*, Cleft Palate-Craniofacial Journal, vol. 29, No. 3, May 1992, pp. 232-238.
Bath, A.P., et al., *Management of Upper Airway Obstruction in Pierre Robin Sequence*, The Journal of Laryngology and Otology, vol. 111, Dec. 1997, pp. 1155-1157.
Brogan, "Rapid maxillary expansion. A stable procedure for improving the nasal airway", Medical Journal of Australia, 1977, vol. 1, No. 6, pp. 167-172.
Coleman, "Suspension sutures for the treatment of obstructive sleep apnea and snoring", Otolaryngologic Clinics of North America, Apr. 1999, 32:2, 277-285.
Cozzi, D.A., et al., *Recurrent Apparent Life-Threatening Event Relieved by Glossopexy*, Journal of Pediatric Surgery, vol. 31, No. 12, Dec. 1996, pp. 1715-1718.
Deluca, "Surgically treatable causes of neonatal respiratory distress", Chilincs in Perinatology, 1978, vol. 5, No. 2, pp. 377-394.
DeRowe, Ari, M.D., et al., *Tongue-Base Suspension with a Soft Tissue-to-Bone Anchor for Obstructive Sleep Apnea: Preliminary Clinical Results of a New Minimally Invasive Technique*, Otolaryngology—Head and Neck Surgery, vol. 122, No. 1, Jan. 2000.
Douglas, Beverly, M.D., *A Further Report on the Treatment of Micrognathia with Obstruction by a Plastic Procedure*, Plastic and Reconstructive Surgery, vol. 5, No. 2, Feb. 1950, pp. 113-122.
Douglas, B., M.D., *The Treatment of Micrognathia with Obstruction by a Plastic Operation*, Department of Surgery, School of Medicine, Vanderbilt University, pp. 420-431.
Faye-Lund, H., et al., *Glossopexia—Evaluation of a new Surgical Method for Treating Obstructive Sleep Apnea Syndrome*, ACTA Otolaryngol (Stockh), 1992, Suppl. 492: pp. 46-49.
Hadley, R.C., M.D., et al., *Utilization of the Kirschner Wire in Pierre Robin Syndrome*, Plastic and Reconstructive Surgery, vol. 31, No. 6, Jun. 1963, pp. 587-596.
Havlik, "Mandibular distraction lengthening in the severely hypoplastic mandible: a problematic case with tongue aplasia", J Craniofac Surg, Nov. 1994, vol. 5, No. 5, pp. 305-310: discussion 311-2.
Hawkins, Donald B., M.D., et al., *Micrognathia and Glossoptosis in the Newborn*, Surgical Tacking of the Tongue in Small Jaw Syndromes, Clinical Pediatrics, vol. 13, No. 12, Dec. 1974, pp. 1066-1073.
Krespi, "Reconstruction after total or subtotal glossectomy", Am J Surg, Oct. 1983, vol. 146, No. 4, pp. 488-492.
Lapidot, Abraham, M.D., *A New Functional Approach to the Surgical Management of Pierre Robin Syndrome: Experimental and Clinical Report*, The Laryngoscope, A Medical Journal for Clinical and Research Contributions In: Otoloaryngology, Broncho-Esophagology, Communicative Disorders, Maxillofacial Surgery, Head and Neck Surgery, Facial Plastic and Reconstructive Surgery, vol. LXXXVI, No. 7, Jul. 1976, pp. 979-983.
Lapidot, Abraham, M.D., et al., *Fastening the Base of the Tongue Forward to the Hyoid for Relief of Respiratory Distress in Pierre Robin Syndrome*, Plastic and Reconstructive Surgery, vol. 56, No. 1, Jul. 1975, pp. 89-91.
Lewis, Stephen R., M.D., et al., *Fascial Slings for Tongue Stabilization in the Pierre Robin Syndrome*, Plastic and Reconstructive Surgery, vol. 42, No. 3, Sep. 1968, pp. 237-241.
Malhotra, "Postural Effects on Pharyngeal Protective Reflex Mechanisms," Sleep, vol. 27, No. 6, 2004, pp. 1105-1112.
Moore, "Mandibular lengthening by distraction for airway obstruction in Treacher-Collins syndrome", J Craniofac Surg, Feb. 1994, vol. 5, No. 1, pp. 22-25.
Moulin, "The challenge of upper airway obstruction in pediatric intensive care", Intensive Care Med., Nov. 1986, 12:412-415.
Oeconomopoulos, Chris, T., M.D., *The Value of Glossopexy in Pierre-Robin Syndrome*, The New England Journal of Medicine, vol. 262, No. 25, Jun. 23, 1960, pp. 1267-1268.
Omur, Mehmet, M.D., et al., *Tongue Base Suspension Combined with UPPP in Severe OSA Patients*, Otolaryngology-Head and Neck Surgery, vol. 133, No. 2, Aug. 2005, pp. 218-223.
Patton, Timothy J., M.D., Joseph H. Ogura, M.D. and Stanley E. Thawley, M.D., "Expansion Hyoidplasty," 1983 First-Place Resident Research Award: Clinical Category, vol. 92, No. 5, Oct. 1984.
PCT International Search Report for PCT-US2007-14342 mailed Sep. 18, 2008.
Piccirillo, Jay F. and Stanley E. Thawley, "Sleep-Disordered Breathing," Cummings: Otolaryngology: Head and Neck Surgery, 3rd ed., Copyright © 1998 Mosby-Year Book, Inc., Chapter 81, pp. 1546-1571.

Rama, Anil N., M.D., MPH, Shivan H. Tekwani, BS and Clete A. Kushida, M.D., Ph.D., "Sites of Obstruction in Obstructive Sleep Apenea," www.chestjournal.org, Oct. 2002.

Ramba, J., *Fixation of the Tongue Bellow Mandible in Pierre Robin Syndrome*, Department for Maxillofacial Surgery, Clinic of Paediatric Stomatology, $2^{nd}$ Medical Faculty, Charles University, Prague, Czech Republic, ACTA Chirurgiae Plasticae 38, 2, 1996, pp. 54-56.

Ramirez, Inferior Sagittal Osteotomy with Hyoid Bone Suspension for Obese Patients with Sleep Apnea, Otolaryngology-Head and Neck Surgery, Sep. 1996, 122:953-957.

Peter Randall, M.D, "The Robin Anomalad: Micrognathia and Glossoptosis with Airway Obstruction, in Reconstructive Plastic Surgery 2241" 2241, 2d ed., W.B. Saunders Co. 1977.

Rawashdeh, Ma'amon A., BDS, MScD, FDSRCS(En), *Surgical Strategies, Transmandibular K-Wire in the Management of Airway Obstruction in Pierre Robin Sequence*, The Journal of Craniofacial Surgery, vol. 15, No. 3, May 2004, pp. 450.

Riley, Current Surgical Concepts for Treating Obstructive Sleep Apnea Syndrome:, J Oral Maxillofac Surg. Feb. 1987, 45: 149-157.

Riley, "Obstructive Sleep Apnea and Hyoid: A revised surgical procedure", Otolaryngology-Head and Neck Surgery, Dec. 1994, 111: 717-721.

Riley, "Obstructive Sleep Apnea Syndrome : A review of 306 consecutively treated surgical patients", Otolaryngology-Head and Neck Surgery, Feb. 1993, 108: 117-125.

Schatten, William E., M.D., et al., *Airway Management in Patients with Pierre Robin Syndrome*, Plastic and Reconstructive Surgery, vol. 38, No. 4, Oct. 1966, pp. 309-311.

Schmitz, "Hyoid Myotomy and Suspension for Obstructive Sleep Apnea Syndrome", J Oral Maxillofac Surg. Nov. 1996, 54: 1339-1345.

Shprintzen, "Pierre Robin, micrognathia, and airway obstruction: The dependency of treatment on accurate diagnosis", International Annesthesiology Clinics., 1988, vol. 26, No. 1, pp. 64-71.

Sjoholm, "Mandibular advancement with dental appliances in obstructive sleep apnoea", J Oral Rehabil, vol. 21, No. 5, Sep. 1994, pp. 595-603.

Waite, "Maxillomandibular advancement surgery in 23 patients with obstructive sleep apnea syndrome", J Oral Maxillofac Surg., Dec. 1989, vol. 47, No. 12, pp. 1256-1261; discussion 1262.

M.R. Wexler, "A Dynamic Fixation of the Base of the Tongue to the Mandible Using De-epithelized Tongue Flap in the Pierre Robin Syndrome", 4 Chirurgia Plastica 297, 1979.

Robert M. Woolf, M.D., "Micrognathia and Associated Cleft Palate, 26 Plastic & Reconstructive Surgery" 199, 1960.

Woodson, "Pharyngeal Suspension suture with Response bone screw for obstructive sleep apnea", Otolaryngology-Head and Neck Surgery, Mar. 1999, 122: 395-401.

Yin, "Mandibular advancement for the treatment of micrognathia with obstructive sleep apnea", Zhonghua Zhueng Xing Shao Shang Wai Ke Za Zhi, vol. 10, No. 4, Jul. 1994, pp. 265-269.

METHODS AND DEVICES FOR THE TREATMENT OF AIRWAY OBSTRUCTION, SLEEP APNEA AND SNORING

The present application claims priority under 35 U.S.C. §119(e) to U.S. Provisional Application No. 60/836,578 filed on Aug. 8, 2006. The present application also claims priority under 35 U.S.C. §120 as a continuation-in-part of U.S. patent application Ser. No. 11/349,040, filed Feb. 7, 2006, which claims priority to U.S. Provisional Application Nos. 60/650,867 filed Feb. 8, 2005 and 60/726,028 filed Oct. 12, 2005. All of the priority applications are hereby incorporated by reference in their entirety.

BACKGROUND

1. Field of the Invention

Certain embodiments of the present invention are related to methods and devices for the treatment of airway obstruction, such as obstructive sleep apnea.

2. Field of the Invention

This invention relates generally to a system and method for treating upper airway obstruction, sleep disordered breathing, upper airway resistance syndrome and snoring by manipulating the structures of the oropharynx, including the tongue.

3. Description of the Related Art

Respiratory disorders during sleep are recognized as a common disorder with significant clinical consequences. During the various stages of sleep, the human body exhibits different patterns of brain and muscle activity. In particular, the REM sleep stage is associated with reduced or irregular ventilatory responses to chemical and mechanical stimuli and a significant degree of muscle inhibition. This muscle inhibition may lead to relaxation of certain muscle groups, including but not limited to muscles that maintain the patency of the upper airways, and create a risk of airway obstruction during sleep. Because muscle relaxation narrows the lumen of the airway, greater inspiratory effort may be required to overcome airway resistance. This increased inspiratory effort paradoxically increases the degree of airway resistance and obstruction through a Bernoulli effect on the flaccid pharyngeal walls during REM sleep.

Obstructive Sleep Apnea (OSA) is a sleep disorder that affects up to 2 to 4% of the population in the United States. OSA is characterized by an intermittent cessation of airflow in the presence of continued inspiratory effort. When these obstructive episodes occur, an affected person will transiently arouse, regain muscle tone and reopen the airway. Because these arousal episodes typically occur 10 to 60 times per night, sleep fragmentation occurs which produces excessive daytime sleepiness. Some patients with OSA experience over 100 transient arousal episodes per hour.

In addition to sleep disruption, OSA may also lead to cardiovascular and pulmonary disease. Apnea episodes of 60 seconds or more have been shown to decrease the partial pressure of oxygen in the lung alveoli by as much as 35 to 50 mm Hg. Some studies suggest that increased catecholamine release in the body due to the low oxygen saturation causes increases in systemic arterial blood pressure, which in turn causes left ventricular hypertrophy and eventually left heart failure. OSA is also associated with pulmonary hypertension, which can result in right heart failure.

Radiographic studies have shown that the site of obstruction in OSA is isolated generally to the supralaryngeal airway, but the particular site of obstruction varies with each person and multiple sites may be involved. A small percentage of patients with OSA have obstructions in the nasopharynx caused by deviated septums or enlarged turbinates. These obstructions may be treated with septoplasty or turbinate reduction procedures, respectively. More commonly, the oropharynx and the hypopharynx are implicated as sites of obstruction in OSA. Some studies have reported that the occlusion begins with the tongue falling back in an anterior-posterior direction (A-P) to contact with the soft palate and posterior pharyngeal wall, followed by further occlusion of the lower pharyngeal airway in the hypopharynx. This etiology is consistent with the physical findings associated with OSA, including a large base of tongue, a large soft palate, shallow palatal arch and a narrow mandibular arch. Other studies, however, have suggested that increased compliance of the lateral walls of the pharynx contributes to airway collapse. In the hypopharynx, radiographic studies have reported that hypopharyngeal collapse is frequently caused by lateral narrowing of the pharyngeal airway, rather than narrowing in the A-P direction.

OSA is generally diagnosed by performing overnight polysomnography in a sleep laboratory. Polysomnography typically includes electroencephalography to measure the stages of sleep, an electro-oculogram to measure rapid eye movements, monitoring of respiratory effort through intercostal electromyography or piezoelectric belts, electrocardiograms to monitor for arrhythmias, measurement of nasal and/or oral airflow and pulse oximetry to measure oxygen saturation of the blood.

Following the diagnosis of OSA, some patients are prescribed weight loss programs as part of their treatment plan, because of the association between obesity and OSA. Weight loss may reduce the frequency of apnea in some patients, but weight loss and other behavioral changes are difficult to achieve and maintain. Therefore, other modalities have also been used in the treatment of OSA, including pharmaceuticals, non-invasive devices and surgery.

Among the pharmaceutical treatments, respiratory stimulants and drugs that reduce REM sleep have been tried in OSA. Progesterone, theophylline and acetozolamide have been used as respiratory stimulants, but each drug is associated with significant side effects and their efficacy in OSA is not well studied. Protriptyline, a tricyclic antidepressant that reduces the amount of REM sleep, has been shown to decrease the frequency of apnea episodes in severe OSA, but is associated with anti-cholinergic side effects such as impotence, dry mouth, urinary retention and constipation.

Other modalities are directed at maintaining airway patency during sleep. Oral appliances aimed at changing the position of the soft palate, jaw or tongue are available, but patient discomfort and low compliance have limited their use. Continuous Positive Airway Pressure (CPAP) devices are often used as first-line treatments for OSA. These devices use a sealed mask which produce airflow at pressures of 5 to 15 cm of water and act to maintain positive air pressure within the pharyngeal airway and thereby maintain airway patency. Although CPAP is effective in treating OSA, patient compliance with these devices is low for several reasons. Sleeping with a sealed nasal mask is uncomfortable for patients. Smaller sealed nasal masks may be more comfortable to patients but are ineffective in patients who sleep with their mouths open, as the air pressure will enter the nasopharynx and then exit the oropharynx. CPAP also causes dry nasal passages and congestion.

Surgical treatments for OSA avoid issues with patient compliance and are useful for patients who fail conservative treatment. One surgery used for OSA is uvulopalatopharyngoplasty (UPPP). UPPP attempts to improve airway patency in the oropharynx by eliminating the structures that contact the tongue during sleep. This surgery involves removal of the uvula and a portion of the soft palate, along with the tonsils and portions of the tonsillar pillars. Although snoring is reduced in a majority of patients who undergo UPPP, the percentage of patients who experience reduced frequency of apnea episodes or improved oxygen saturation is substantially lower. Postoperatively, many patients that have undergone UPPP continue to exhibit oropharyngeal obstruction or concomitant hypopharyngeal obstruction. Nonresponders often have physical findings of a large base of tongue, an omega-shaped epiglottis and redundant aryepiglottic folds. UPPP is not a treatment directed at these structures. UPPP also exposes patients to the risks of general anesthesia and postoperative swelling of the airway that will require a tracheostomy. Excessive tissue removal may also cause velopharyngeal insufficiency where food and liquids enter into the nasopharynx during swallowing.

Laser-assisted uvulopalatopharyngoplasty (LAUP) is a similar procedure to UPPP that uses a CO2 laser to remove the uvula and portions of the soft palate, but the tonsils and the lateral pharyngeal walls are not removed.

For patients who fail UPPP or LAUP, other surgical treatments are available but these surgeries entail significantly higher risks of morbidity and mortality. In genioglossal advancement with hyoid myotomy (GAHM), an antero-inferior portion of the mandible, which includes the attachment point of the tongue musculature, is repositioned forward and in theory will pull the tongue forward and increase airway diameter. The muscles attached to the inferior hyoid bone are severed to allow the hyoid bone to move superiorly and anteriorly. Repositioning of the hyoid bone expands the retrolingual airspace by advancing the epiglottis and tongue base anteriorly. The hyoid bone is held in its new position by attaching to the mandible using fascia. Variants of this procedure attach the hyoid bone inferiorly to the thyroid cartilage.

A laser midline glossectomy (LMG) has also been tried in some patients who have failed UPPP and who exhibit hypopharyngeal collapse on radiographic studies. In this surgery, a laser is used to resect the midline portion of the base of the tongue. This involves significant morbidity and has shown only limited effectiveness.

In some patients with craniofacial abnormalities that include a receding mandible, mandibular or maxillomandibular advancement surgeries may be indicated for treatment of OSA. These patients are predisposed to OSA because the posterior mandible position produces posterior tongue displacement that causes airway obstruction. In a mandibular advancement procedure, the mandible is cut bilaterally posterior to the last molar and advanced forward approximately 10 to 14 mm. Bone grafts are used to bridge the bone gap and the newly positioned mandible is wire fixated to the maxilla until healing occurs. Mandibular advancement may be combined with a Le Fort I maxillary osteotomy procedure to correct associated dental or facial abnormalities. These procedures have a high morbidity and are indicated only in refractory cases of OSA.

Experimental procedures described in the clinical literature for OSA include the volumetric radiofrequency tissue ablation and hyoidplasty, where the hyoid bone is cut into several segments and attached to a brace that widens the angle of the U-shaped hyoid bone. The latter procedure has been used in dogs to increase the pharyngeal airway lumen at the level of the hyoid bone. The canine hyoid bone, however, is unlike a human hyoid bone because the canine hyoid bone comprises nine separate and jointed bones, while the human hyoid bone comprises five bones that are typically fused together.

Notwithstanding the foregoing, there remains a need for improved methods and devices for treating obstructive sleep apnea.

SUMMARY OF THE INVENTION

Methods and devices for manipulating tissue are provided. A tissue-tensioner is used to tension a region of tissue. The tissue tensioner is used to engage certain tissue of the body and apply tension to those tissues.

In further embodiments, methods and devices are disclosed for manipulating the tongue. A tissue engaging structure is positioned on the tongue, and the device can be manipulated to displace at least a portion of the posterior tongue in an anterior or lateral direction, or to alter the tissue tension or compliance of the tongue.

In one embodiment, disclosed is a method for treating a condition of an airway, including the steps of: providing a securement mechanism configured to be attached to a patient's mandible, the securement mechanism comprising one or more adjustment mechanisms; passing one or more sutures through a tongue to form a suture loop, at least a portion of the suture loop passing laterally through the tongue; securing the one or more sutures relative to the patient's mandible with the securement mechanism, wherein the one or more sutures engage the one or more adjustment mechanisms and the securement mechanism is secured to the patient's mandible; and adjusting the tension in the suture loop by manipulating the one or more adjustment mechanisms. In some embodiments, the securement mechanism comprises a bone screw attached to the mandible. In some embodiments, the suture loop may include either: a first suture portion and a second suture portion engaged with a second adjustment assembly, or a first suture portion engaged with a first adjustment assembly and a second suture portion engaged with a second adjustment assembly. In some embodiments, the one or more adjustment assemblies comprise one or more adjustment spools. In some embodiments, the securement mechanism is attached to the patient's mandible before either passing one or more sutures through the tongue to form a suture loop, or engaging the one or more sutures with the one or more adjustment mechanisms. In some embodiments the one or more sutures engage the one or more adjustment mechanisms before attaching the securement mechanism to the patient's mandible.

In another embodiment, disclosed is a tissue tensioner for suspending the tongue that includes a suture loop comprising one or more sutures configured to suspend the tongue with at least one portion configured to extend laterally through the tongue; and a securement mechanism configured to be attached to a patient's mandible. The securement mechanism preferably includes one or more adjustment mechanisms for engaging the one or more sutures and adjusting tension on the suture loop. In some embodiments the securement mechanism includes a bone screw attached to the mandible. In some embodiments, the first suture loop comprises one of the following: a first suture potion and a second suture portion both engaged with a single adjustment assembly, or a first suture portion engaged with a first adjustment assembly and a second suture portion engaged with a second adjustment assembly. In some embodiments the one or more adjustment assemblies includes one or more adjustment spools.

In another embodiment disclosed is a method for treating a condition of an airway that includes the steps of providing a securement mechanism configured to be attached to a patient's mandible; providing a plurality of elongate members, the elongate members each being connected to a tissue anchor; attaching the plurality of tissue anchors to a tongue; connecting the plurality of elongate members to the securement mechanism; and securing the securement mechanism to the mandible. In some embodiments, securing of the securement mechanism to the mandible occurs either before or after connecting the plurality of elongate members to the securement mechanism. In some embodiments the securement mechanism is secured to the inferior portion of the mandible. In some embodiments the plurality of elongate members could include any of the following: tethers, beaded tethers, active variable length tethers, a biocompatible coating, or a tissue ingrowth surface. In some embodiments, the elongate members have tissue anchors connected thereto, the tissue anchors attached to the tongue on both lateral sides of the tongue. In some embodiments the securement mechanism is secured to a mandible at or near the midpoint of the mandible. In some embodiments the method further includes adjusting the tension or length of the elongate member using an adjustment assembly operably attached to the elongate member.

In another embodiment, disclosed is a tissue tensioner for suspending the tongue, including a securement mechanism configured to be attached to a patient's mandible and a plurality of elongate members, the elongate members each being connected to a tissue anchor; wherein the tissue anchors are configured to be connected to lateral portions of the tongue and the elongate members are configured to be connected to the securement mechanism. The securement mechanism can be a clamping interface. The elongate member can include any one of the following: a tether, an elastic tether, a biocompatible coating applied to at least some parts of a tether, a tissue engaging surface, or a beaded tether.

In yet another embodiment, disclosed is a method for treating a condition of an airway, the method including the steps of providing a tissue tensioner comprising an elongate member and a hyoid anchor connected to the elongate member configured to engage and grip a surface of a hyoid bone; providing a securement mechanism configured to be attached to a patient's mandible; engaging the hyoid bone with the hyoid anchor; connecting the elongate member to the securement mechanism; and securing the securement mechanism to the mandible. Securing the securement mechanism can occur before or after connecting the elongate member to the securement mechanism. In some embodiments, the elongate member can include any of the following: a tether, an elastic tether, an active variable length tether, a biocompatible coating applied to at least some parts of the elongate member, or a tissue engaging surface. In some embodiments the securement mechanism includes an adjustment mechanism, and could also include the step of adjusting tension on the elongate member between the mandible and the hyoid bone. In still other embodiments, the hyoid anchor can include at least one bar for engaging an upper ridge of the hyoid bone, or a first relatively straightened configuration and a second relatively curved configuration, wherein the step of engaging the hyoid bone with the hyoid anchor includes transforming the hyoid anchor to the second relatively curved configuration.

In yet another embodiment disclosed is a tensioner for treating a condition of an airway including an elongate member and a hyoid anchor connected to the elongate member configured to engage and grip a surface of a hyoid bone; and a securement mechanism configured to be attachable to a patient's mandible, the securement mechanism being connectable to the elongate member. In some embodiments the elongate member can include any of the following: a tether, an elastic tether, a biocompatible coating applied to at least some parts of a tether, a tether with a tissue engaging surface, or a beaded tether. In yet still other embodiments the securement mechanism can include an adjustment mechanism. In yet other embodiments the hyoid anchor includes either: at least one barb for engaging an upper ridge of the hyoid bone or a first relatively straightened configuration and a second relatively curved configuration.

DETAILED DESCRIPTION OF THE PREFERRED EMBODIMENTS

Causes of airway obstruction include but are not limited to obstructive sleep apnea, snoring and congenital disorders such as Pierre-Robin syndrome. Disclosed herein are various embodiments of devices and methods for treating causes of airway obstruction. Embodiments described herein relate to, for example, adjustability, improved tethers, and improved anchoring of those implants to treat said conditions. Such devices and methods are further described in co-pending application Ser. No. 11/349,040, filed Feb. 7, 2006 and published Sep. 14, 2006 as U.S. Patent Publication No. 2006-0201519A1 ("Frazier '519 publication") as well as in U.S. Pat. No. 5,988,171 to Sohn et al. (herein, "Sohn") and U.S. Pat. No. 6,161,541 to Woodson (herein "Woodson"). Disclosed embodiments herein may also be adapted for use with the REPOSE® System by InfluENT Medical (Concord, N.H.).

U.S. patent application Ser. No. 11/349,040, filed Feb. 7, 2006 and published Sep. 14, 2006 as U.S. Patent Pub. No. 2006-0201519 A1 ("Frazier '519 publication"); U.S. Provisional Patent Application No. 60/813,230, filed Jun. 13, 2006 ("'230 provisional application"); U.S. Provisional Patent Application No. 60/813,285, filed Jun. 13, 2006 ("'285 provisional application); U.S. Patent Application No. 60/813,058, filed Jun. 13, 2006 ("'058 provisional application"); U.S. Patent Publication No. 2005/0092334 to Conrad et al ("Conrad"); U.S. Pat. No. 6,250,307 to Conrad et al. ("Conrad '307"); U.S. patent application Ser. No. 11/762,642 filed Jun. 13, 2007 ("Dineen '642 application"); U.S. patent application Ser. No. 11/762,752 filed Jun. 13, 2007 ("Hirotsuka '752 application"); and U.S. patent application Ser. No. 11/762,652 filed Jun. 13, 2007 ("Jackson '652 application"); U.S.

Pat. No. 5,988,171 to Sohn; and U.S. Pat. No. 6,161,541 to Woodson are all incorporated by reference herein in their entirety.

U.S. Patent Publication No. 2005/0126563 to van der Burg et al. (the van der Burg '563 publication) which is incorporated by reference in its entirety, discloses additional systems and methods for treating airway obstruction, for example, by manipulation of the hyoid bone. Embodiments or particular elements of embodiments disclosed herein may also be used in combination with embodiments or particular elements of embodiments disclosed in Publication No. 2005/0126563.

Securement Assemblies

Bone anchors utilized with the disclosed methods and devices are preferably self tapping and/or self-drilling bone screws having a head which is crimped onto the suture. A hole, preferably axial, is provided in the head of the screw for securing the suture. The head of the screw is crimped to both secure the suture and provide a non-circular shape to the rear end of the anchor. This non-circular head can be driven by a correspondingly shaped socket of a power driver. Typically, one or two separate sutures providing 1, 2, 3, 4 or more strands or loops of suture, may be crimped to the screw. The screw may include an axial notch in its distal portion such that the screw is self-drilling. In a preferred embodiment, as illustrated in FIG. 1A of Sohn, bone screw 20 includes a generally conical distal portion 22 having an external, spiral thread 24, and a generally cylindrical proximal portion 26. The thread 24 preferably has a substantially greater diameter than proximal portion 26, for reasons that will be described below. Proximal portion 26 includes an axial hole 28, which receives a suture. The suture itself is preferably secured to the screw 20 using a crimping operation, such as a suture illustrated in FIGS. 2A and 2B of Sohn.

A tongue suspension system such as disclosed in Sohn, as well as the hyoid distraction and/or suspension system of Woodson can include various securement assemblies (also referred to as securement mechanisms herein), such as those disclosed in the Frazier '519 publication (e.g., securement mechanisms illustrated in FIGS. 40-51 of the Frazier '519 publication) replacing the bone anchors described in Sohn and Woodson. The securement mechanism may be configured to hold one or more sutures as disclosed in Sohn or Woodson, or, in other embodiments, one or more tethers disclosed in the Frazier '519 application. The disclosed embodiments advantageously allow for the installation of the securement mechanism prior to attachment of sutures or tethers to the securement mechanism. In contrast, the sutures are pre-attached to the bone screw in Sohn and Woodson. Pre-attached sutures may undesirably hinder implantation of the bone screw by physically interfering with the surgical field.

Figure 1:
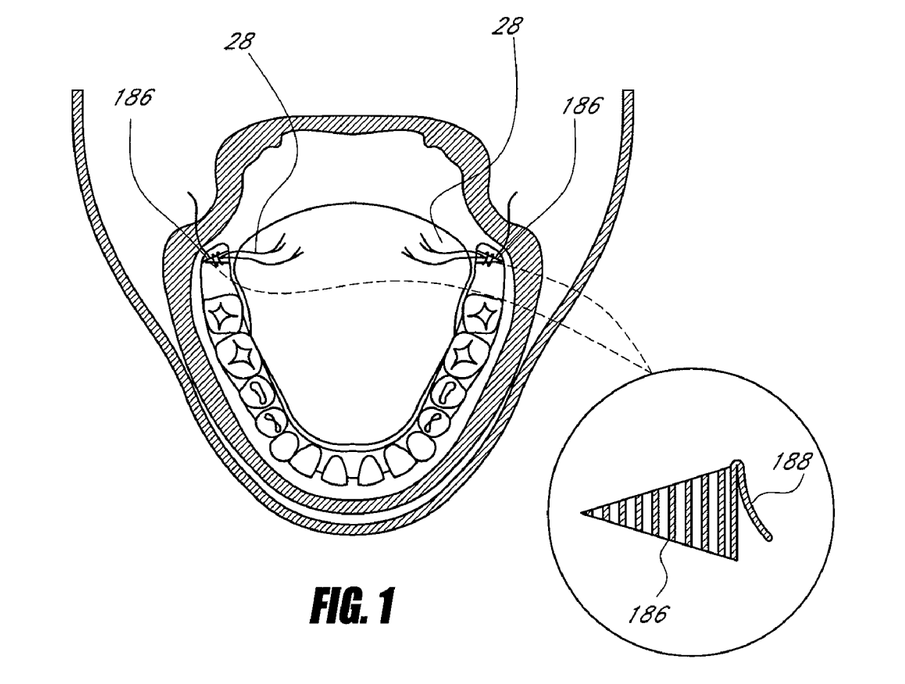
FIG. 1 is a schematic diagram showing various non-limiting examples of securement assemblies that may be used with a tongue or hyoid suspension system, according to one embodiment of the invention.

In one embodiment, illustrated schematically in FIG. 1 herein, the tongue 5290 or hyoid (not shown) suspension system of Sohn or Woodson respectively comprises a bone anchor 186 with a clamping interface 188 for retaining tethers 28, as illustrated in connection with FIGS. 40A-C of the Frazier '519 publication. While two lateral bone anchors 186 are shown in FIG. 1, various other locations are possible, including a single midline bone anchor 186 in other embodiments. The clamping interface 188 comprises two opposing surfaces 190, 192 or structures that are adapted to provide a frictional or mechanical interface with tethers or other elongate members inserted within the clamping interface 188. The clamping interface 188 has an open configuration depicted in FIGS. 40B and 40C of the Frazier '519 publication to allow positioning of one or more tethers within the interface 188 and a closed configuration shown for retaining the tethers. The closed configuration may be achieved by crimping the two opposing surfaces 190, 192 or by further structures of the clamping interface, such as complementary clasps or clip structures to fix the opposing surfaces 190, 192 together. As shown in FIG. 40C of the Frazier '519 publication, the clamping interface 188 may further comprise complementary indentations 194 and protrusions 196 to further enhance the frictional resistance of the interface in the closed configuration. The opposing surfaces or structures of the clamping interface may also be configured with frictional surfaces that are well known in the art through the use of various materials, surface treatments or configurations. Frictional surface configurations may also include cross hatched surfaces or irregular porous surfaces.

In other embodiments, the bone screw or securement assembly may be placed through an insertion site inferior to the mandible and preferably but not necessarily about the anterior portion of the mandible. The bone screw or securement assembly may be secured to the inferior or inner surface of the mandible. The submandibular approach may be advantageous, for example, in creating a more aesthetically desirable result post-implantation.

Adjustment Mechanisms

The tongue suspension system disclosed in Sohn and the hyoid distraction and/or suspension system of Woodson may also include one or more adjustment elements, such as those disclosed in the Frazier '519 publication (e.g., those adjustment elements illustrated in FIGS. 61A-K of the Frazier '519 publication), the '230 provisional application (e.g., those illustrated in FIGS. 73-108 of the '230 provisional application), or the Dineen '642 application. Adjustment elements can advantageously allow for adjusting the tension of the sutures disclosed in Sohn after implantation of the tongue or hyoid suspension system, or the mandible-hyoid suture tension as disclosed in Woodson. A tongue remodeling system, device, and/or method for treating a patient with breathing problems that can be adjusted before, during and/or after the initial implantation procedure may be better tolerated and less prone to treatment failure. For example, by being able to adjust the tension or bias of the sutures disclosed in Sohn and Woodson by methods other than by cutting and re-tying the sutures, at times other than during implantation, suture migration, suture extrusion, and/or dysphagia may be avoided or corrected.

Figure 2:
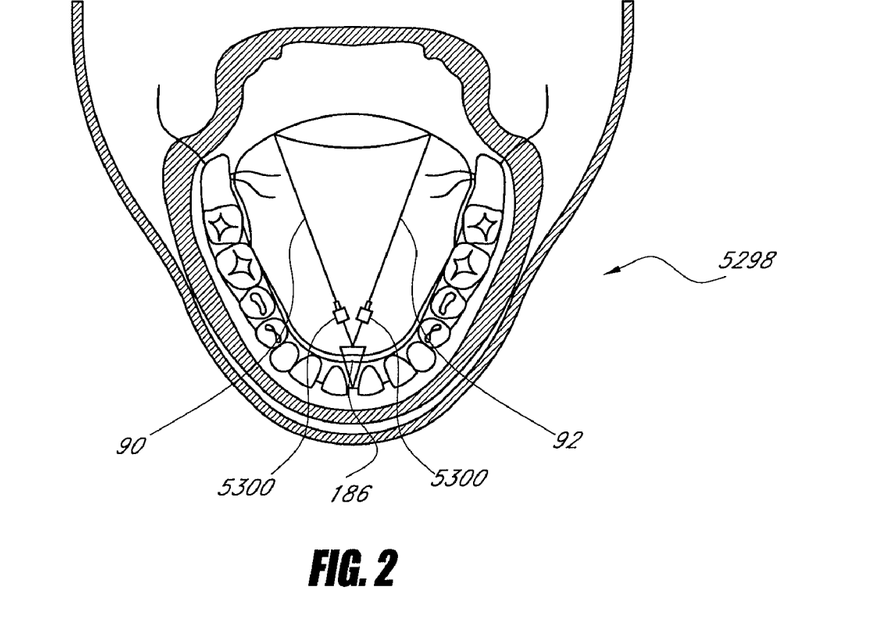
FIG. 2 illustrates a tongue suspension system including adjustment elements to adjust the tension of a tether, according to one embodiment of the invention.

In one embodiment of the invention, illustrated schematically in FIG. 2 herein, the improved tongue suspension system 5298 comprises one or more spools or rotation assemblies 5300, such as a spool assembly 5300 illustrated in FIGS. 61A to 61I of the Frazier '519 application, for adjusting the suture length or tether tension between the mandibular screw 186 and one, or both of the sutures 90, 92. A suture having portions 90, 92 is looped from a single bone screw 186, to the base of the tongue. The suture can then be extended laterally across the tongue base, and then back to the bone screw 186 as shown. In some embodiments, there can be a single bone screw, or a common location where multiple adjustment assemblies are located. A preferred system 5298 as shown in FIG. 2 advantageously has dual adjustment assemblies 5300, 5300 such that each side of the tongue can be individually tensioned. Patients with asymmetric tongue anatomy or tissue ingrowth post-implantation may especially benefit from a system having multiple adjustment assemblies 5300.

The hyoid distraction or suspension system disclosed in the Woodson '541 patent can similarly be improved by the addition of one or more adjustment elements described in the Frazier '519 publication, the '230 provisional application, or the Dineen '642 application, as noted above. For example, an adjustment element can be installed at any point along the suture between the hyoid bone and the mandible screw disclosed in various embodiments of Woodson to thus adjust the suture tension and correspondingly, the pharyngeal space.

Tethers

As disclosed in Sohn and Woodson, after attachment of one or more sutures to at least one bone screw, the bone screw is inserted into the mandible. The suture(s) are then used to pull the tongue forward to clear the patient's airway. The sutures can be attached to one bone anchor or to two bone anchors, as desired. The suture(s) are preferably under the skin at all points, although it is not necessary to achieve successful results.

The tongue or hyoid suspension system disclosed in Sohn and the hyoid distraction and/or suspension system disclosed in Woodson can be improved by replacing the sutures disclosed with one or more of the tethers disclosed in the Frazier '519 publication (e.g., those illustrated in FIGS. 27-38 of the Frazier '519 publication), the '285 provisional application, (e.g., those illustrated in FIGS. 73-84 of the '285 provisional application), or the Hirotsuka '752 application and configured for use with the aforementioned tongue or hyoid suspension systems. As noted in the Frazier '519 publication, a tether with elastic properties or comprising structures that provide a length/tension relationship may be preferred in some instances. A tether capable of lengthening in response to increased load or tension may be optimized to provide sufficient bias to reduce the effects of oropharyngeal occlusion while providing a more physiologic range of tongue motion than that produced by fixed length tethers. Fixed length glossoplasty or suspension of the tongue may be the cause of odynophagia, dysphagia and deglutition problems seen with existing tongue remodeling devices, but the current invention is not limited to this purpose. A tether with elastomeric properties may be provided by using materials such as but not limited to urethane or silicone. One skilled in the art can select the particular material, tether length, diameter, cross-sectional shape and other features based upon the desired effect, tolerances, and the particular patient's anatomical characteristics. Other materials that may comprise the tether include but are not limited to Nitinol, spring steel, tantalum, polyethylene, polyester, silk, polypropylene, polyolefin or a combination thereof.

Other tether configurations that may be used include passive and active variable length or bias structures such as braided or woven structures, electropolymers, springs, coils, magnets or solenoids. Thus, in some of the embodiments, the tether configuration may actively change in length or configuration resulting from the application of external energy or force such as electrical current or magnets. These active tether configurations may be further configured with local or distal sensor components that may modulate the activity of the external energy or force acting on the active tether. The modulation may be influenced or triggered by detection of diaphragm movement or depolarization activity, nerve depolarization, pressure changes and/mechanical contact in the airway.

The tether may also be covered by a lubricious biocompatible coating. In another embodiment, the tether comprises a bioabsorbable coating that may cause scar or connective tissue formation about the tether. Scar tissue formation may further enhance the effect of the glossoplasty implant by tightening the tongue tissue and/or to resist migration of the implant.

In some embodiments, a tether of a tissue engaging member may be configured with one or more structures or surfaces capable of engaging at least a portion of the tissue surrounding the tether so that an anchor is not required, or to distribute the tissue engagement. In still other embodiments, the tissue-engaging member may comprise multiple distal anchors and multiple tethers arranged in a serial or branching fashion.

Figure 3:
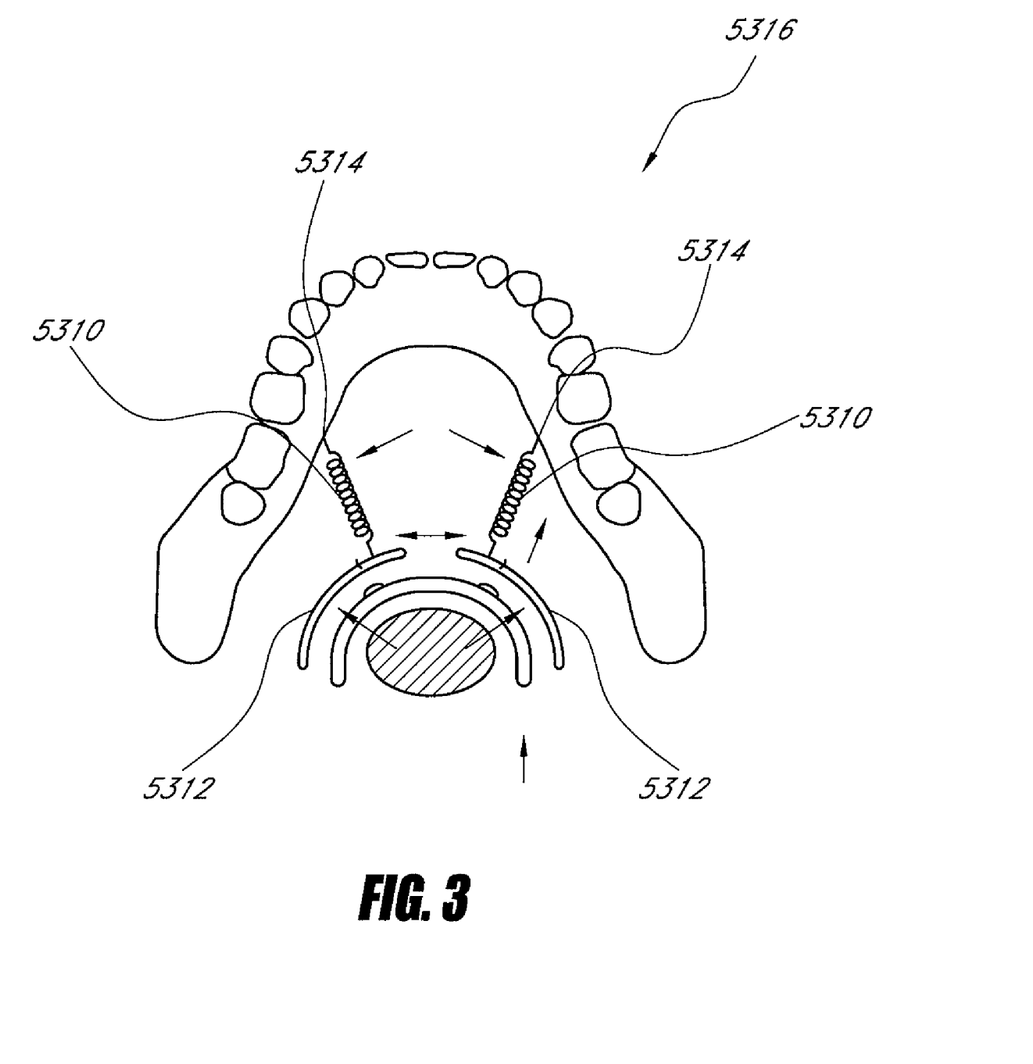
FIG. 3 shows a hyoid distraction and suspension system including a plurality of elastomeric tethers, according to one embodiment of the invention.

FIG. 3 herein illustrates an embodiment of an improved hyoid distraction and suspension device 5316. The device can be as illustrated in FIG. 3 of Woodson, except that the sutures described in Woodson are replaced with elastomeric tethers 5310 connecting portions of the hyoid bone 5312 to the respective bone screws 5314. In other embodiments, one or more tethers 5314 selected from the tethers disclosed in the Frazier '519 publication, the '285 provisional application, or the Hirotsuka '752 application replace the sutures described in Woodson.

Figure 4:
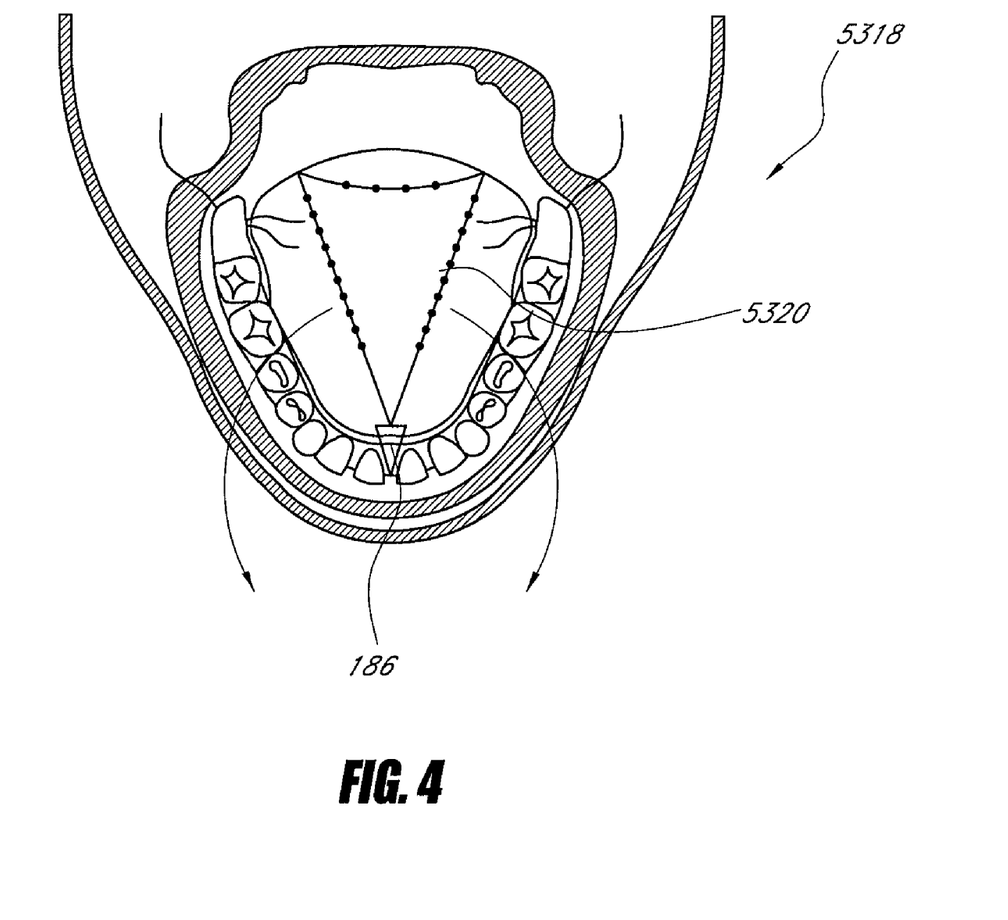
FIG. 4 illustrates a tongue suspension system that includes a tether with a beaded configuration, according to one embodiment of the invention.

FIG. 4 herein illustrates an embodiment of an improved tongue suspension device. The device is as illustrated in FIG. 9E of Sohn, except that the sutures described in Sohn are replaced with a beaded tether 5320. The beaded tether 5320 may advantageously promote tissue in-growth and better tension the tongue suspension system 5318. In other embodiments, one or more tethers 5320 selected from the tethers disclosed in the Frazier '519 publication, the '285 provisional application, or the Hirotsuka '752 application replace the sutures described in Woodson.

As illustrated in FIG. 5, in one embodiment, an improved tongue suspension system 5060 comprises a tether further comprising one or more "sling" elements 5062 on, for example, a suture-based tongue advancement device, such as disclosed in Sohn. The sling element 5062 may comprise, for example, a batten of porous fabric, woven material, a large diameter suture, braid, band, and the like. The sling element 5062 may be operably connected to one or more sutures, as disclosed in Sohn and illustrated, for example, in FIG. 9E of Sohn. In some embodiments, the sling element 5062 comprises a central lumen configured to receive one or more sutures within the lumen. The sling element 5062 may alleviate trauma during installation of the tongue suspension system 5060 because the enlarged suture portion need not be passed through the entire tongue T. The sling element 5062 may also advantageously increase anchoring surface area in the tongue T and prevent undesired migration of the sutures.

Figure 5A:
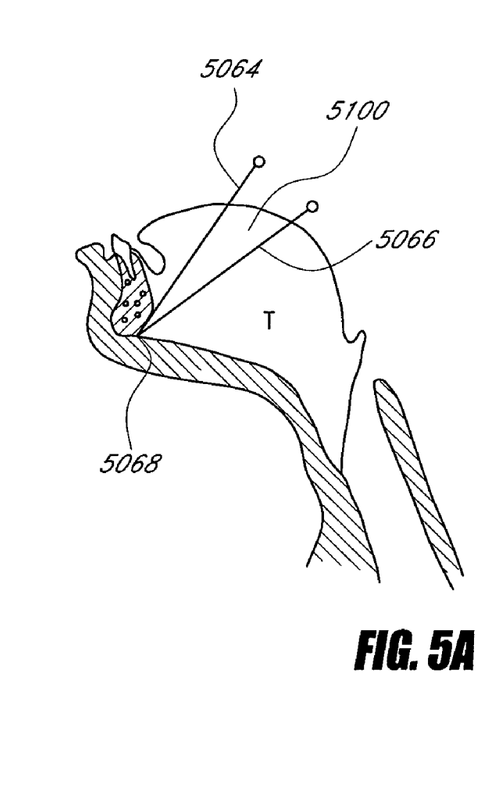
FIGS. 5A-C depict a tongue suspension system comprising a multi-piece sling, according to one embodiment of the invention.
Figure 5B:
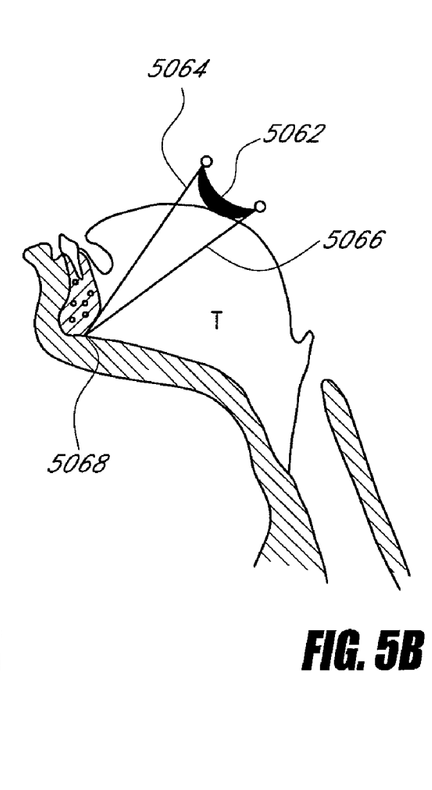
Figure 5C:
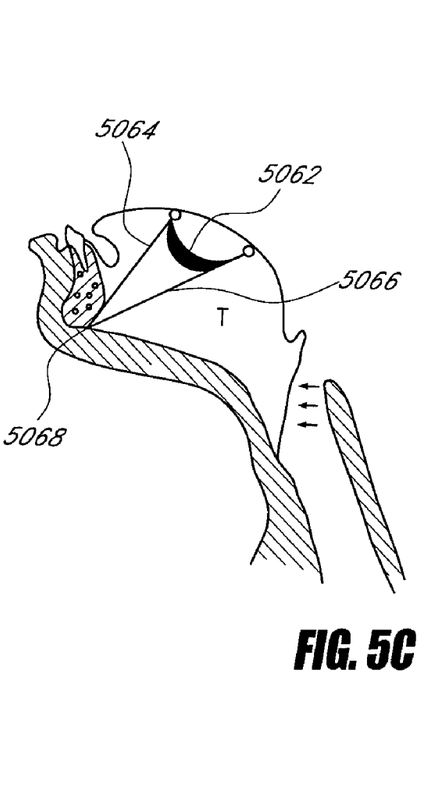

A method of deploying an improved tongue suspension system 5060 comprising a sling element 5062 is disclosed herein and illustrated in FIGS. 5A-5C. The method comprises the step of passing a first suture 5064 through the genioglossus muscle 5100 exiting the dorsum lateral to the midline. Next, a second suture 5066 is passed through the genioglossus muscle 5100 exiting the dorsum lateral to the midline on the contralateral side. Next, a sling element 5062 is passed under the tongue T surface between exit holes created from the passing of the first 5064 and second 5066 sutures through the genioglossus muscle 5100. Then, sutures 5064, 5066, are attached to each end of the sling element. In some embodiments comprising a sling element 5062 further comprising a lumen, the sutures may be secured within the lumen of the sling element 5062. The sutures 5064, 5066 may then be attached to the bone anchor 5068. In another embodiment, the sling element 5062 is formed during the procedure by passing a plurality of sutures transversely through the tongue along different pathways. The ends of the sutures located to each side of the midline tongue are then joined together to form the ends of the sling element. The in situ formed sling element can then be attached to the first and second sutures as described above.

Tissue Engagement

A method for anterior suspension of the tongue is illustrated in Sohn, for example, in FIGS. 9A-E. A suture 32 operably connected at one end 90 is passed posteriorly through one side of the base of the tongue, shown in FIG. 9B of Sohn. As shown in FIG. 9C of Sohn, the end 90 of suture 32 is next passed laterally, through the other posterior side of the base of the tongue 76. A second suture section 94 of suture 92 is folded to form a loop 96. It is also passed through the base of the tongue 76 from front to back, so as to meet the end 90 of suture 32. The end 90 of the first suture 32 is passed through the loop 96. Alternatively, suture 94 may be first passed through the base of the tongue, and then the end 90 of the suture 32 may be passed laterally through the base of the tongue and through the loop 96. Next, the suture section 94 is drawn anteriorly out of tongue 76, thus pulling the end 90 of suture 32 forward through the tongue, until suture 32 emerges in proximity to screw 20, as shown in FIG. 9D of Sohn. Ends 90, 92 of suture 32 are tied together in a knot 98, shown in FIG. 9E of Sohn, with a tension sufficient to provide a desired degree of suspension of the tongue. Preferably, suture 32 is then drawn through the tongue so that knot 98 is pulled unobtrusively under the tongue where it will not disturb the patient.

Figure 6:
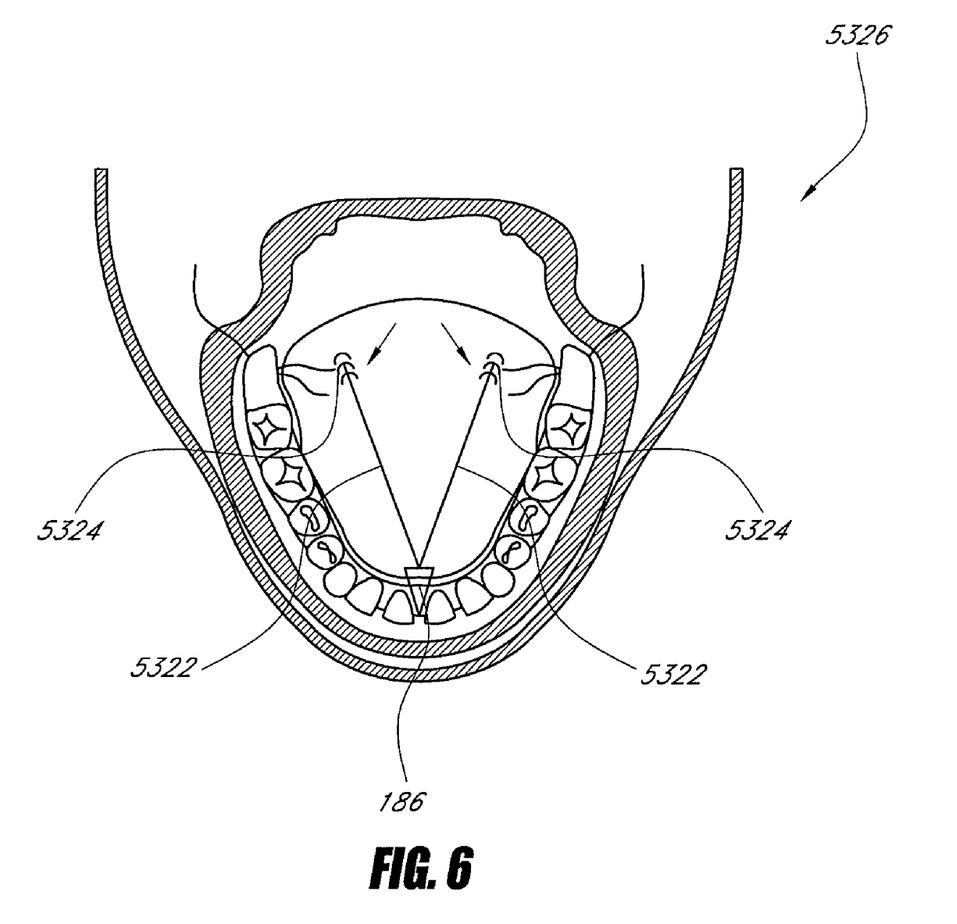
FIG. 6 shows a tongue suspension system with a plurality of distal anchors, according to one embodiment of the invention.

In one embodiment of the invention, as illustrated in FIG. 6, one or more tissue engaging members (e.g., tissue anchors), as described in the Frazier '519 publication (e.g., as illustrated in FIGS. 7-26 of the Frazier '519 publication), the '058 provisional application (e.g., as illustrated in FIGS. 73-112 of the '058 provisional application), or the Jackson '652 application, illustrated schematically in FIG. 6 herein, replaces a suture loop as described in Sohn. The tissue engaging members 5324 of the tongue suspension system 5326 can advantageously improve tongue suspension by providing a greater surface area and resistance to migration of the system 5326 relative to the sutures disclosed in Sohn, and thus can better prevent pain from undesired excess migration, dysphagia, or extrusion of the system. The anchor or anchors 5324 may be placed posteriorly at one or, both lateral sides of the tongue where the sutures are passed as disclosed in Sohn. The anchor 5324 may be operably connected to a suture 5322, a tether as disclosed in the Frazier '519 publication, the '258 provisional application, or the Jackson '752 application, as noted above. In other embodiments, one or more anchors 5324 may be placed may be placed at any point along the suture or tether 5322 line to improve tongue suspension (e.g., beads on the tethers). In some embodiments, the tissue-engaging members are located at an end of the tether. Also shown is a securement mechanism 186 operably connected to ends of tethers 5322. While depicted as placed within the mandible near the midline, securement mechanisms 186 may also be located at other locations, such as laterally as shown in FIG. 1, or in other bony or soft tissue structures as described herein as well.

Figure 7A:
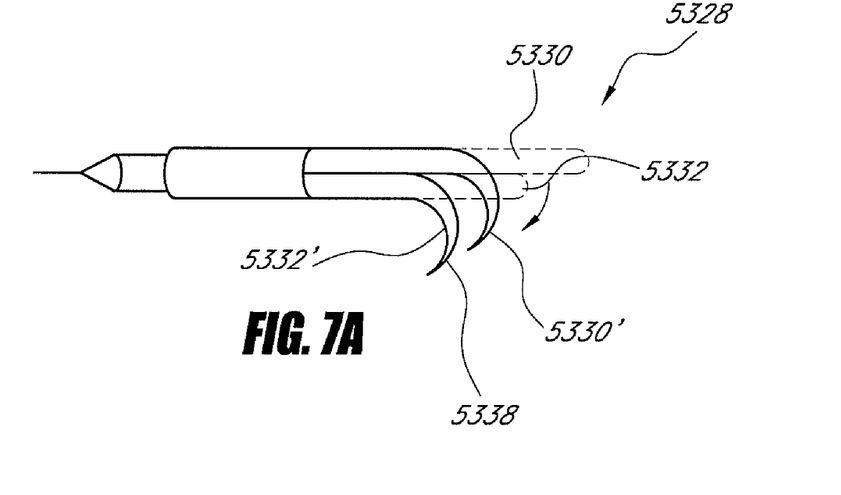
FIGS. 7A-B illustrate a hyoid anchor, according to one embodiment of the invention.

FIG. 7A of Sohn illustrates a procedure for anterior suspension of the tongue involving the hyoid bone of the patient. A first screw is inserted into the mandible, and a second screw is driven into the hyoid bone. The screw may have either one or two sutures that can be tied together to pull the hyoid bone forward toward the mandible and to simultaneously suspend the base of the tongue.

Figure 7B:
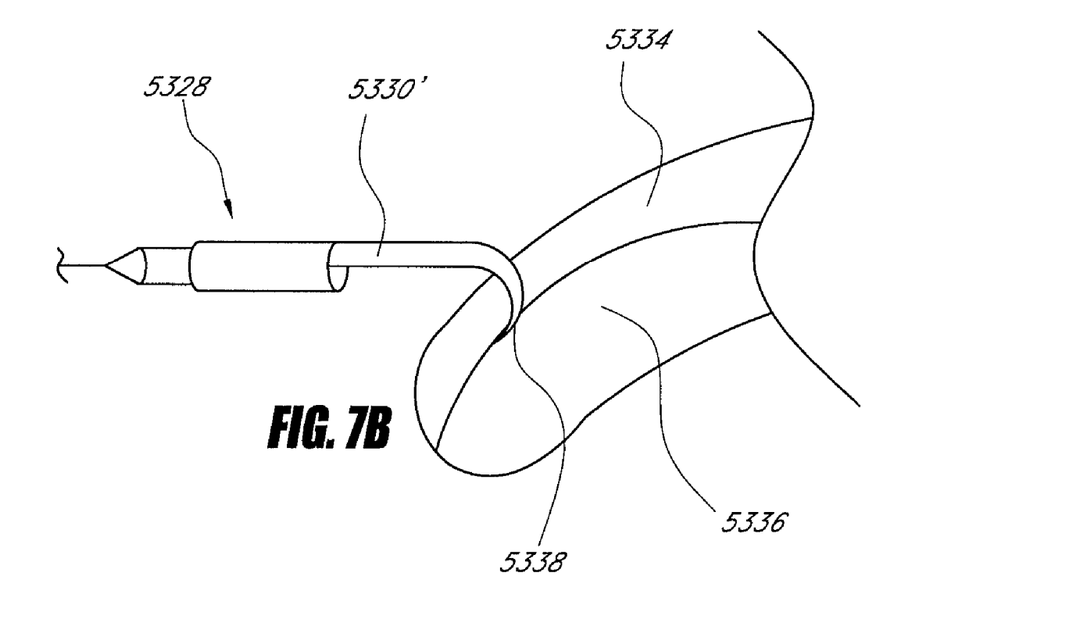

FIG. 7B of Sohn illustrates another tongue and hyoid suspension procedure. In this procedure, sutures that are attached to screws in the mandible are passed intraorally around the hyoid bone. Preferably, two screws are inserted, one above the other, generally at the midline of the mandible. The suture attached to the lower screw passes below and behind the hyoid bone, generally along a sagittal axis at the midline of the bone, while the suture attached to the upper screw of the screws passes above the hyoid bone on this axis. These sutures are preferably passed above and below the mylohyoid muscle, adjacent to the hyoid bone and are tied together to suspend the hyoid bone to the screws in the mandible.

FIGS. 3A-3D of Woodson illustrate a hyoid distraction procedure. The procedure first involves inserting two bone screws approximately 3-4 cm posterior to the anterior midline along the inferior border of the mandibular body about the level of the digastric fossa of the mandible. Looped ends of polypropylene sutures attached to the bone screws are loaded onto a suture passer. The sutures are passed inferiorly under the subcutaneous tissues to exit at a point just above the hyoid bone. The procedure may then be repeated on the contralateral side, following which the sutures are released from the passer. The hyoid bone is then split at the midline with a sagittal saw into left and right halves. A fixation device is then used to separate the divided ends of the body of the hyoid bone. After sawing the bone, the right-sided loop of polypropylene suture is cut to make two separate strands of suture. One strand is loaded onto an appropriately sized Mayo needle. This suture is passed around the right portion of the split hyoid, from the superior portion of the hyoid to emerge at the hyoid's inferior portion. This is then repeated again on the right side, creating a two-strand wraparound of the suture from the hyoid's superior to inferior portion. After completion of the two-strand wraparound on the right side, this procedure is repeated for the left side of the split hyoid, with the second set of sutures. The suture strands are then tied with an appropriate tension by changing the amount of wraparound of the suture on the hyoid. The surgical field is then closed as further disclosed in Woodson. Alternatively, hyoid suspension may be performed without splitting of the hyoid bone.

An improved hyoid suspension device and method is illustrated herein in FIGS. 7A-7B comprising a hyoid anchor 5328 in lieu of the hyoid screw and suture elements disclosed in Sohn, or the hyoid suture loop disclosed in Woodson. The hyoid anchor 5328 comprises one or more barbs 5330', 5332' that are curved in a first direction. The barbs 5330', 5332' preferably are configured to engage the upper ridge 5334 of the hyoid bone 5336. In some embodiments, the barbs 5330', 5332' can comprise grip-like finger projections 5338 at their distal end to better engage the upper ridge 5334 of the hyoid bone, as shown in FIG. 7B, with a single barb 5330'. In other embodiments (not shown), the barbs 5330', 5332' can extend to engage the entire height of the hyoid bone 5336 (as opposed to the upper ridge 5334) to minimize the stress on the bone. To facilitate deployment of the hyoid anchor 5328, the barbs may have a first substantially straightened configuration 5330, 5332 during deployment, and a second, curved configuration 5330', 5332' after deployment. The anchor 5328 may be transformed from the first to the second configuration, for example, manually, or the use of a shape memory material, such as Nitinol. Use of an anchor 5328 as described that engages an outer surface of the hyoid bone, e.g., the upper ridge, may reduce trauma and risk of fracture of the hyoid bone 5326 that exists by driving a screw into the hyoid bone 5326. In some embodiments, the anchor 5326 is configured to be transformed back from the second 5330', 5332' to the first configuration 5330, 5332 to facilitate the later removal of the hyoid engagement system 5328, if desired.

In other embodiments, the anchor may engage the peri-hyoid tissue instead of engaging the hyoid bone. Preferably, the peri-hyoid tissue is tissue that is anterior to the hyoid bone. The anchors described in the Frazier '519 publication and the Jackson '652 application may be configured and sized to engage the anterior peri-hyoid tissue.

In other embodiments, the hyoid anchor described herein may be used to open the pharyngeal space instead of the suture tied around the distracted or suspended hyoid bone as illustrated in FIGS. 3A-3D of Woodson.

Figure 8:
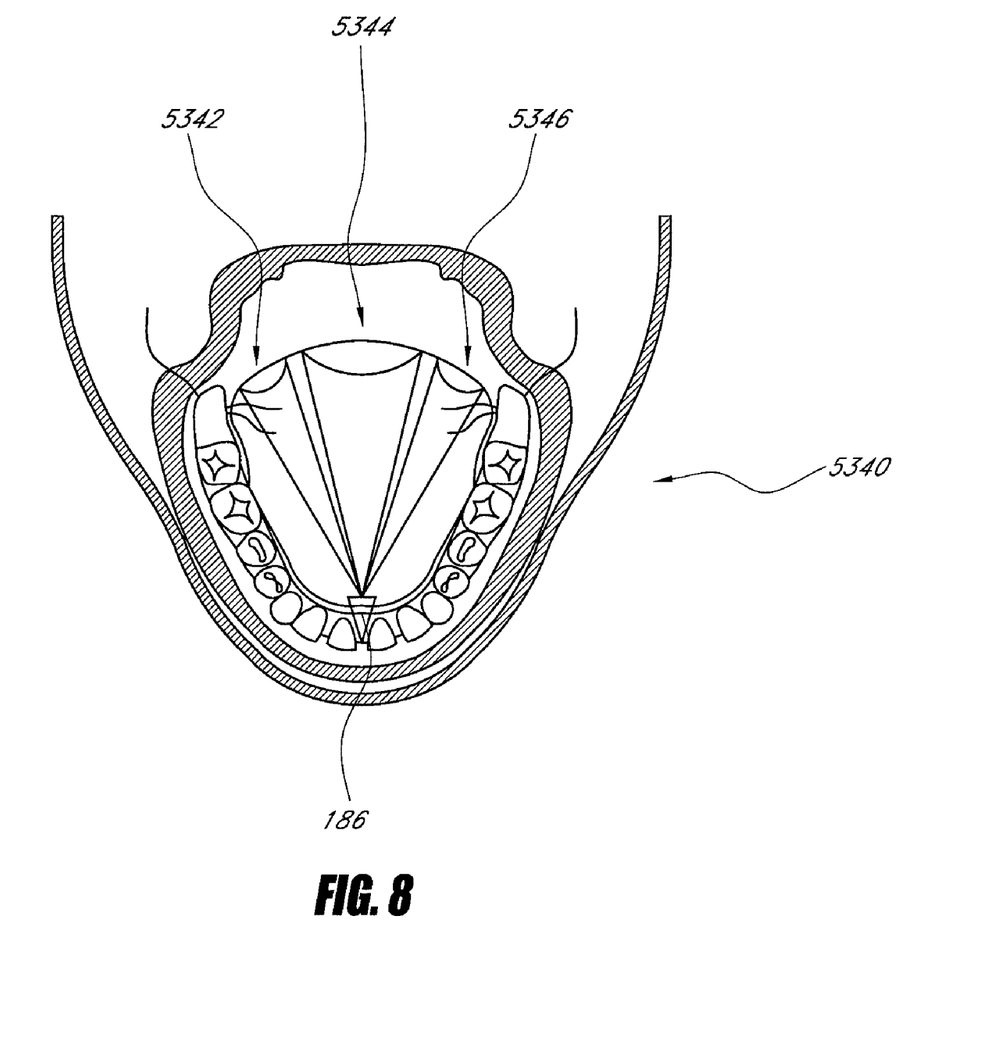
FIG. 8 shows multiple tongue suspension devices within a tongue suspension system, according to one embodiment of the invention.

As illustrated in FIG. 8, shown is an improved tongue suspension system 5340 having a plurality of tongue suspension assemblies 5342, 5344, 5346, such as the tongue assembly described in Sohn. The assemblies may share a common bone anchor 186 suspending the tongue with one or more sutures as in Sohn (or a variety of tethers as described above), or alternatively may have separate bone anchors. A plurality of tongue suspension assemblies 5342, 5344, 5346 can be advantageous, for example, in patients with jaw or tongue asymmetries such that one assembly may be tensioned with a force different from the contralateral side. In some embodiments, a tongue suspension system may comprise at least about two, three, four, five, or more tongue suspension assemblies.

In another embodiment, a method for placing an improved tongue suspension system, such as any of the embodiments described herein or the REPOSE® System, is disclosed. First, after induction of general nasotracheal or endotracheal anesthesia, the patient is placed in the semi-Fowler's or tonsillectomy position with a shoulder roll in place. The patient may be prepped and draped in the normal manner. Next, a mouth guard element may be placed in the mouth between upper and lower molar teeth for exposure. A local anesthetic, such as lidocaine with epinephrine 1/100,000 may be administered in the floor of the mouth. An optional retraction tether, such as a No. 1 silk suture, may be placed through the tongue tip to aid in retracting the tongue forward during the procedure.

The intra-oral anterior mandible is palpated and the insertion site of a bone screw or other securement mechanism, such as the securement mechanisms disclosed in the Frazier '519 publication, is determined at the level of the genioglossal tubercle below the roots of the teeth. Optionally, another incision may be made at the base of the frenulum. Local anesthetic is preferably injected at the insertion area. The securement mechanism may be inserted into the floor of the mouth in the midline posterior to the Wharton's ducts orifices.

Using the optional No. 1 silk suture or tether at the tongue apex, the tongue is then retracted to expose the floor of the mouth. A suture that may comprise polypropylene, or a tether, such as that disclosed in the Frazier '519 publication, the '285 provisional application, or the Hirotsuka '752 application, may be passed (for example, with the aid of a suture passer disclosed in Sohn) through the initial insertion hole or incision in the mouth floor, through the tongue, and aiming for a midway point between the foramen cecum and vallecula at the posterior area of the tongue base and 1-2 cm lateral to the midline. The tongue may then be retracted anteriorly. The looped suture or tether pass is then continued from the anterior portion of the tongue to the posterior base of the tongue, exiting 1-2 cm lateral to the midline of the posterior tongue at a level of midway between the foramen cecum and the vallecula, avoiding the neurovascular bundle.

Atraumatic forces may then be used to grasp and hold the loop suture or tether, and the suture or tether may be pulled and tagged with an atraumatic clamp, its exit point used as a reference for the contralateral suture or tether pass. There is now a looped suture or tether protruding from the posterior base of the tongue.

One of the tether ends may then be passed from the anterior insertion hole in the floor of the mouth to the posterior base of the tongue, exiting 1-2 cm lateral to the midline, on the contralateral side of the previously inserted suture loop, and at the same horizontal level.

The screw suture or tether protruding from the posterior tongue base may then attached to a #10 mayo needle or similar tether passer and a submucosal pass is made through the exit point of the tether, to the contralateral side through the exit hole of the looped tether and this screw tether is then threaded through the looped tether which is still protruding from the posterior base of the tongue.

The looped tether may then be pulled forward, toward the anterior portion of the tongue dragging the tether anteriorly towards the floor of the mouth and insertion site of the screw. A triangular tether pass through the tongue has now been achieved.

The suture or tether ends are now tied together, bringing the posterior tongue based forward approximately 3-7 mm. Holding the surgical knot to tension, the posterior base of the tongue is then palpated, a tension band and a small dimple can be felt at the posterior base of the tongue. The knot may then be secured, buried, and the incision or anchor defect closed with an absorbable suture. The aim of the surgical procedure is to provide support, which will prevent backwards prolapse of the posterior tongue base when a patient is in the supine position, rather than tongue advancement while the patient is awake.

The suture or tether, once tied, suspends the posterior base of the tongue 3-7 mm forward, preventing the posterior tongue base from collapsing in the pharyngeal space during sleep. In time, the suture or tether material may become encased in fibrous tissue lending long term support and rigidity of the airway. Providing and installing one or more adjustment elements as disclosed in the Frazier '519 publication, '230 provisional application, or the Dineen '642 application (which may be, for example, operably connected to the securement mechanism, or along the length of the suture or tether), to the tongue suspension system disclosed herein can facilitate post-implantation adjustment of the tension of the tether on the system.

In other embodiments, one variation on the aforementioned method of placing a tongue suspension system involves making the initial incision at a site inferior to the mandible (a submandibular approach), preferably but not always about the anterior portion of the mandible, as illustrated in FIGS. 4A-4D of the Frazier '519 publication. The bone screw or other securement mechanism may be secured to the inferior or inner surface of the mandible to reduce visibility of the securing assembly beneath the skin. Other elements of the tongue suspension system, such as the sutures or tethers, anchors, and the like may be passed, through, for example, a piercing delivery tool known in the art, through the initial submandibular incision. In other embodiments, the implantation pathway may originate from a location anterior or lateral to the mandible, and in still other embodiments, may also pass through the mandible.

While this invention has been particularly shown and described with references to embodiments thereof, it will be understood by those skilled in the art that various changes in form and details may be made therein without departing from the scope of the invention. For example, in some embodiments, a tongue or hyoid suspension device may have one or more elements of embodiments described herein, for example, one or more anchors disclosed in the Frazier '519 publication, the '058 provisional application, or the Jackson '652 application and one or more adjustment elements described in the Frazier '519 publication, '230 provisional application, or the Jackson '652 application. Furthermore, the invention encompasses other combinations of any or all of the disclosures of the aforementioned references. For all of the embodiments described above, the steps of the methods need not be performed sequentially.

We claim:

1. A method for treating a condition of an airway, comprising:
    attaching a securement mechanism to a patient's mandible, the securement mechanism comprising one or more adjustment mechanisms;
    passing one or more sutures through a tongue to form a suture loop, at least a portion of the suture loop passing laterally through the tongue;
    after attaching the securement mechanism to the patient's mandible, securing the one or more sutures relative to the patient's mandible by attaching the one or more sutures to the securement mechanism, wherein the one or more sutures engage the one or more adjustment mechanisms; and
    adjusting tension in the suture loop by manipulating the one or more adjustment mechanisms.

2. The method of claim 1, wherein the securement mechanism comprises a bone screw attached to the mandible.

3. The method of claim 1, wherein the suture loop comprises a first suture portion and a second suture portion both engaged with a first adjustment assembly.

4. The method of claim 1, wherein the suture loop comprises a first suture portion engaged with a first adjustment assembly and a second suture portion engaged with a second adjustment assembly.

5. The method of claim 1, wherein the one or more adjustment assemblies comprise one or more adjustment spools.

6. The method of claim 1, wherein the securement mechanism is attached to the patient's mandible before passing one or more sutures through the tongue to form a suture loop.

7. The method of claim 1, wherein the securement mechanism is attached to the patient's mandible before engaging the one or more sutures with the one or more adjustment mechanisms.

8. A method for treating a condition of an airway in a patient, comprising:
    providing a securement mechanism configured to be attached to a patient's mandible, the securement mechanism comprising one or more adjustment mechanisms;
    passing one or more sutures through the patient's tongue to form a suture loop, at least a portion of the suture loop passing laterally through the tongue;
    after passing the one or more sutures through the tongue, securing the one or more sutures relative to the patient's mandible by attaching the one or more sutures to the securement mechanism, wherein the one or more sutures engage the one or more adjustment mechanisms; and
    adjusting tension in the suture loop by manipulating the one or more adjustment mechanisms.

9. The method of claim 8, wherein the securement mechanism comprises a bone screw attached to the mandible.

10. The method of claim 8, wherein the suture loop comprises a first suture portion and a second suture portion both engaged with a first adjustment assembly.

11. The method of claim 8, wherein the suture loop comprises a first suture portion engaged with a first adjustment assembly and a second suture portion engaged with a second adjustment assembly.

12. The method of claim 8, wherein the one or more adjustment assemblies comprise one or more adjustment spools.

13. The method of claim 8, wherein the securement mechanism is attached to the patient's mandible before passing one or more sutures through the tongue to form a suture loop.

* * * * *